United States Patent
Keim et al.

(10) Patent No.: US 6,589,478 B1
(45) Date of Patent: Jul. 8, 2003

(54) DISINFECTING FLAT SURFACES WHICH FORM ROOMS, USING WATER VAPOR

(75) Inventors: Bettina Keim, Munich (DE); Martin Schaffer, Lenzfrieder Strasse 15, D-80637 Munich (DE)

(73) Assignees: Genoveva Beurer, Munich (DE); Martin Schaffer, Munich (DE)

( * ) Notice: Subject to any disclaimer, the term of this patent is extended or adjusted under 35 U.S.C. 154(b) by 0 days.

(21) Appl. No.: 09/646,482

(22) PCT Filed: Mar. 12, 1999

(86) PCT No.: PCT/DE99/00691

§ 371 (c)(1),
(2), (4) Date: Sep. 15, 2000

(87) PCT Pub. No.: WO99/59644

PCT Pub. Date: Nov. 25, 1999

(30) Foreign Application Priority Data

Mar. 17, 1998 (DE) .......................................... 198 11 587

(51) Int. Cl.[7] .................................................. A61L 4/00
(52) U.S. Cl. .............................. 422/26; 422/27; 422/28; 422/31; 422/33; 422/292; 422/295; 422/297
(58) Field of Search ............................. 422/26, 27, 28, 422/31, 33, 292, 295, 297

(56) References Cited

FOREIGN PATENT DOCUMENTS

| DE | 41 08 538 A1 | 9/1992 |
| EP | 0 827 709 A2 | 3/1998 |
| EP | 1 064 028 B1 | 12/2001 |

*Primary Examiner*—Krisanne Thornton
(74) *Attorney, Agent, or Firm*—Birch, Stewart, Kolasch & Birch, LLP

(57) ABSTRACT

The invention relates to a device for carrying out the process, which enables the disinfection of flat and enclosing surfaces using steam.

In order to achieve this, a disinfection head 1, which exhibits a nozzle assembly 3 and a suction bell 6, is connected to a holder 2 such that it can move.

The holder has an inlet hose 13 to enable the steam to be introduced into the disinfection head and an outlet suction hose 7. The inlet hose is connected to an initial evaporator cell 9 and the outlet suction hose is connected to a collection container 8. The initial evaporator cell, the collection is container, the suction pumps and the necessary valves and heating elements are joined together in a mobile unit 23.

18 Claims, 5 Drawing Sheets

DISINFECTING FLAT SURFACES WHICH FORM ROOMS, USING WATER VAPOR

BACKGROUND OF THE INVENTION

1. Field of the Invention

2. Description of the Background Art

The invention relates to a process and a device for carrying out the disinfection of flat and enclosing surfaces using steam, which comes into contact with the surfaces to be disinfected.

Surfaces are disinfected in a number of different ways in order to avoid the transferral of undesirable pathogenic micro-organisms to humans and animals. The most common method is disinfection using chemicals, the use of which, together with the prescription of antibiotics in the past, has been associated with environmental problems, and is also increasingly leading to the development of higher levels of resistance to micro-organisms.

This means that, especially in hospitals, there is increasing concern about the development of multi-resistant disease pathogens, which no longer react in the desired way to various disinfectants or combinations thereof.

Another recognized method which is mostly used for smaller objects, such as medical instruments, is heat disinfection. However, this requires such long times and high temperatures to be effective that its application in many areas is either impractical or economically unviable, especially where enclosing surfaces are concerned.

Therefore, a disinfection device which works simply and without the use of harmful chemicals and which adequately removes all pathogenic and undesirable micro-organisms would be useful in a number of places where hygiene plays a crucial role, such s as hospitals, canteens, animal holding and storage centers for food manufacturers and sanitary areas.

There are indications that a technically simple, cost-effective steam cleaning method could be considered as a new method of disinfection. The example applications published to date work on the assumption that the temperature and the pressure of a steam cleaner have a disinfecting effect providing the time is measured properly.

Most of the advertising statements about alleged disinfection effects made in the past by various manufacturers have had to be withdrawn because the disinfection results tested at random did not stand up to closer scientific scrutiny and therefore did not fulfil the requirement of reliability which is crucial to any disinfection process.

A doctorate commenced in 1994 at the Institut for Tierhygiene, Verhaltenskunde und Tierschutz [institute for animal hygiene, behavioural science and animal welfare] at the Ludwig-Maximilian University in Munich investigated steam cleaning as a potential method of disinfection.

The results of these investigations were published at the 6th Hohenheim Seminar from Sep. 23–24, 1996 by A Haas, S Platz and J Unshelm, in a presentation on the subject of "Environment and animal hygiene". The results showed that the effective time required for the use of steam, which had been calculated on the basis of results for thermal disinfection, could actually be drastically reduced to 5–10 seconds. However, these results relied on the apparatus tested (Uninova Hausgeräte GmbH) which had specific technical characteristics including a cloth stretched over the steam outlet and a minimum distance of 2.5 cm from the cloth to the specimen slide. The results were only achieved under laboratory conditions, and did not answer the question as to whether the system could be applied in practice on an economically viable basis, especially for relatively large surfaces.

Patent specification DE 41 08 538 A1 describes a process for heat disinfection of surfaces, especially sealed areas through which an agent could flow. During the process described, a heated medium which forms a mist and is capable of flowing is brought into contact with the surfaces to be disinfected. The is specifications suggest that a pipe connected with the pathogen Pseudomonas aeriginosa was free of bacteria after only a few minutes of contact with steam, as the mist-forming medium, at a temperature of between 70 and 90° C.

This process is primarily used for rinsing out pipes with steam, and not for the heat disinfection of relatively large surfaces using water alone (as detailed above), as the above patent specification suggests that the disinfectant could also be added to the water or that the disinfectant could be used alone.

An illustration of the way that steam cleaners work, published by B Bullemer on Nov. 15, 1993 to clarify the scientific background, comes to the conclusion that the reaction that supplies the energy for steam cleaning is the recombination of steam molecules into water. A hypothermic energy supply from condensing steam was proposed as an alternative disinfection method by the same source on Apr. 10, 1995.

However, the fact that it cannot be assumed that the user has adequate knowledge of the principles of thermodynamics proved to be a major problem. Even the aforementioned doctorate to explain the disinfecting effect of steam cleaners does not go into detail on the physical principles at work and the publication detailed presents the results of experiments under laboratory conditions, although external conditions which are constantly changing, such as those that can be caused by different temperatures or pressures on different surfaces, are not taken into consideration.

SUMMARY OF THE INVENTION

Therefore, the aim of the invention is to provide a process and a device to carry out the process, as described at the beginning, such as to enable cost-effective disinfection of flat and enclosing surfaces with as short as possible an effective time for the superheated steam used and to increase significantly the levels of reliability under application conditions which are constantly changing, thus increasing the range of applications to as many micro-organisms as possible.

In order to achieve this aim, the invention proposes guiding the steam through a specially designed disinfection head. The disinfection head should be movable, connected to the inlet hose for the steam via a holder with a handle, then connected via a preliminary chamber to a nozzle assembly which maintains a distance of 2.5 cm (considered to be the optimum distance) from the surface to be disinfected and forms a steam chamber with the front section of the housing of the disinfection head.

The disinfection head is surrounded by a suction bell and sucks away the condensed steam produced via suction nozzles on the disinfection head.

The suction nozzles flow into a joint outlet suction hose inside the plastic holder holding the disinfection head and take the condensed material to a collection container, from where it is again, taken back to the initial evaporator cell of the device and sterilized.

An important element of the disinfection head is the nozzle assembly through which the steam is guided such that when it reaches the surface to be disinfected, it does not contain a drop of liquid water.

The nozzle assembly controls the main flow of steam by initially retarding it and then distributing it on a surface which can be used economically.

At the same time, the nozzle assembly prevents the steam coming out onto the surface to be disinfected at too high a pressure, causing unnecessary disruption to the micro-organisms. The fact that the flow of steam is split up into a number of steam channels increases the number of condensation processes in the steam chamber. As a multiple of the average heat energy of the boiling point of water is discharged onto the disinfection surface, which is riddled with micro-organisms, for every condensation process, an increased number of openings through the nozzle assembly improves the utilization of energy, which is critical to the success of the disinfection process.

It transpired that the effective time could be reduced if the number of openings was increased. The results were checked on test cultures of Staphylococcus aureus and Pseudomonas aeruginosa under the following variable external environmental conditions and on different surfaces: wooden surfaces in cold stores at temperature of 6° C., metal surfaces in operating theaters at a temperature of 17° C. and under artificially generated pressure, and plastic surfaces, which had been roughened up by the use of chemicals, in air shafts in a sterile area used for the production of food at a temperature of 23° C.

A further development of the invention is proposed whereby the nozzle assembly, in conjunction with the aforementioned disinfection head, provides adequate disinfection and also reduces the effective time required for the steam to under 3 seconds.

For this, the nozzle assembly is approximately 2.5 cm thick and is made of 4 plates which join together to form a holder. The four plates are separated by gaps of approximately 1 mm, which are filled with the horizontal openings for flows of steam. Again, some of the kinetic energy of the steam flowing through is converted, and, after the opening of the outlet, it is available in the front steam chamber in the form of electromagnetic energy for the actual disinfection process.

The horizontal openings cover the whole surface, but are distributed evenly at 7 mm apart, they have a vacuum coated metal surface and an opening diameter of 0.5 mm.

Overall, an opening area of approx. 4 pro mille for a nozzle assembly surface proved to be very effective as steam opening area. As the disinfecting effect of silver in water has long been known, and, in comparison to other materials tested, it, also has the best surface resistance against the steam flowing through, silver was used for the coating of the openings.

In a further embodiment of the invention, it is proposed that the nozzle assembly or its plates, which are made of a ceramic material or heat-resistant plastic, be heated. The energy required can be introduced via a line inside the holder. In a further development of the invention, it is proposed that the external surfaces of the nozzle assembly which come into contact with the steam and the horizontal internal surfaces of the gaps separating the plates be coated with another precious metal, preferably gold or platinum. The benefits of this coating are essentially that both precious metals have proven suitable for processing in composites with ceramic or plastic materials and silver-coated openings, they are also resistant to corrosion and exhibit neither visible wear nor deformity after prolonged use.

Although steam generally dries without leaving any residue, series of experiments have shown that, with uncoated plastic or ceramic surfaces, the openings blocked up after about two hours of use, and the internal and external surfaces of the nozzle assembly exhibited increased coating which hampered the otherwise precise development of the laminar flow. The results when other metals were used were similarly undesirable, therefore gold and platinum give the best reaction results in the longer term. In a further embodiment of the invention, the disinfection head is not rectangular with the nozzle assembly adapted accordingly, as in the original version, rather an oval disinfection head is proposed which exhibits a cylindrical nozzle assembly with dimensions of approx. 2.5×7 cm, in a round opening. A section opening in the disinfection head accommodates the suction channel. This embodiment is designed to use the aforementioned principle of condensing steam to disinfect places which are difficult to access, such as joints and folds.

Once it has surrounded the round nozzle assembly, the oval disinfection head goes into a tapering nozzle which is about 2.5 cm long.

As a further embodiment, this oval nozzle can be straight, bent with various angles of inclination or curved around more than 250°. This sort of design would be suitable for disinfecting suspended ceiling components which are accessible through holes.

The opening for the suction channel begins around 0.7 cm before the end of the nozzle.

In a further embodiment of the invention, it is proposed that the condensed steam produced is sucked off and led back into the initial evaporator cell. There is an advantageous embodiment where the rectangular disinfection head described above is enclosed by a suction bell, preferably made of transparent plastic. In its basic design, the suction bell is adapted to the external shape of the disinfection head and exhibits rotating sliding bearings or rollers in the area where it comes into contact with the area to be disinfected, making the user's work easier and protecting both the surfaces and the disinfection head. The sliding bearings have only a negligible effect on the distance between the nozzle assembly and the surfaces.

There are suction nozzles with a lateral opening angle of around 135° to the disinfection head on the narrow side and/or below the disinfection head. These flow into suction channels, which should preferably meet inside the holder and form into a single suction outlet which leads into a collection container.

In an appropriate embodiment of the invention, it is proposed that the suction function is controlled by means of a sliding and/or toggle switch arranged on the plastic holder and operated by the user using his thumb, whereby one function is used for suction, the other for steam.

An optical signal on the disinfection head also makes sense. In a particularly advantageous embodiment of the invention, it is proposed that any surviving micro-organisms are sucked away and removed as part of the suction process. It makes sense to suck the condensed steam through a coarse filter and a fine filter into a collection container which should be smaller in volume than the volume of the initial evaporator cell. The collection container and the initial evaporator cell are amalgamated in a single device, whereby the collection container is easily removable and can be disinfected by the system itself.

It is also planned to bring the condensed material collected in the collection container via a second suction pump and a pipe into the (initial) evaporator cell, where the condensed material, including any micro-organisms dissolved in it, and any surviving micro-organisms, is automatically sterilized by reheating it at the working pressure required.

Once the reheating process is complete, the steam is fed back to the disinfection head.

A particular advantage of this device lies in the fact that even heat-resistant micro-organisms, such as spore-producing ones, are also eliminated without having to increase the short effective time of the steam after carrying out the first stage of the process, as described above, a factor which is very important from the point of view of economic viability. The sterilization phase therefore increases the range of micro-organisms on which the device is effective and therefore its area of application.

There is an additional benefit in the fact that toxic substances released when the cell membranes are destroyed are made harmless, which also improves user safety.

It is also advantageous that the initial evaporator cell exhibits a boiler outlet screw which is accessible to the user and can therefore be cleaned inside on a regular basis. A particular advantage of the invention lies in the reduced amount of water required and the extended period for which it can work, as a result of the fact that the disinfection and sterilization systems are combined in a single device. Additional chemicals are also superfluous. A further advantage lies in the high level of acceptance among users in hospitals and animal hygiene, where sterilization has been standard practice for a long time and where the procedure can be seamlessly integrated into existing disinfection processes. It also provides an effective, hygienic and safe solution to parasite attacks and removal of parasites (and, for example, their eggs) in the food industry. Overall the procedure suggested fulfils all the requirements of a disinfection process. It is reliable, cost-effective, harmless in terms of materials, user-friendly and has a wide range of applications, to which it provides quick and irreversible results. It is also harmless to humans and the environment.

It is also possible to use the process to which the invention relates to carry out disinfection and subsequent sterilization of surfaces and objects where hygiene is particularly important, such as respiration systems, cardiac and circulation equipment, catheters, general medical instruments, operation sluices, labor wards, intensive care units and infection wards.

If required, the disinfection head can be made larger than shown in the drawing in order to use larger nozzle assemblies and disinfect larger areas in a shorter space of time.

BRIEF DESCRIPTION OF THE DRAWINGS

Further advantages and details of the invention are revealed in the following description of a few example embodiments and on the basis of the simple diagrams, wherein:

FIG. 4 a) shows a view of an oval version of the disinfection head b) shows a view of a round disinfection head c) shows a view of curved nozzle shapes.

DETAILED DESCRIPTION OF THE PREFERRED EMBODIMENT

Figure 1:
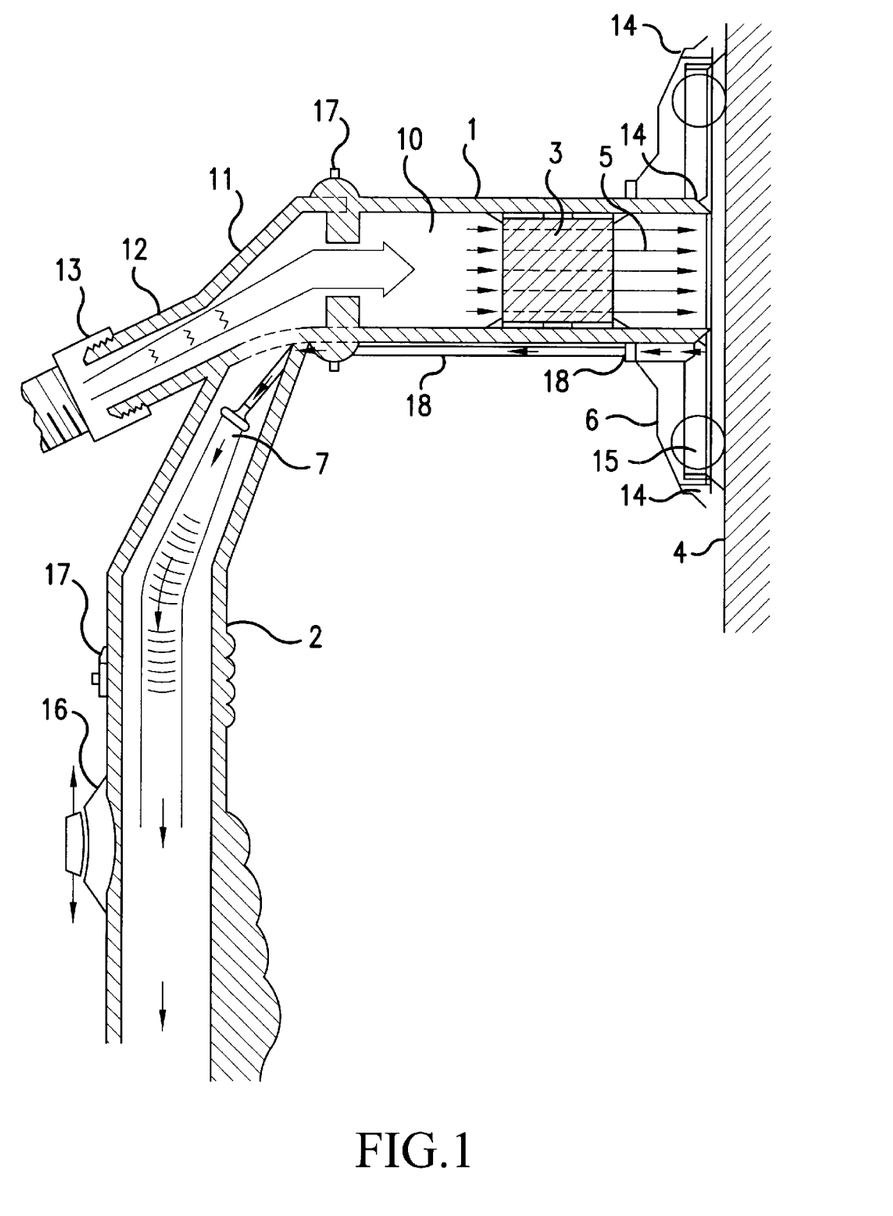
FIG. 1 shows a cross-section of a disinfection head complete to with a nozzle assembly, a holder, a inlet steam hose, a suction bell, a disinfection surface and an outlet suction hose.

FIG. 1 shows a special embodiment of a disinfection head 1 held by a plastic holder 2 and in the center of which is a preliminary chamber 10 and a nozzle assembly 3 through which the steam emitted from a steam inlet spout 12 is guided such that it lands on the surface 4, to be disinfected opposite the nozzle assembly with as few drops of water as possible and with a laminar flow. The nozzle assembly 3, together with the front section of the housing of the disinfection head 1 and the surface to be disinfected 4, forms a steam chamber 5 which is largely sealed, in which the evaporation energy releases its disinfecting effect. The suction bell 6 takes in the condensed steam and the micro-organisms dissolved therein and sucks it away via suction channels 18 to the side of or below the disinfection head 1 into the center of the plastic holder 2. Where the suction bell 6 comes into contact with the surface, there are rotating sliding bearings 15 in a suspension system in order to even out unevenness in the surface and to keep the disinfection head 1 at the right distance from the surface to be disinfected 4. The suction bell 6 also has a brush crown or a moveable plastic band 14. The switch 16 on the plastic holder 2 can trigger the steam inlet by being pressed forward, and can have either a slider or a toggle action. When the steam is activated, a light 17 displays the time the steam will need to take effect. Moving the switch back again triggers the suction of the steam. The steam is fed in and sucked away through different systems of hoses in order to make the suction system easier. Various different disinfection heads can also be attached to the plastic holder 2 and can be moved by means of a ball-joint.

Figure 2:
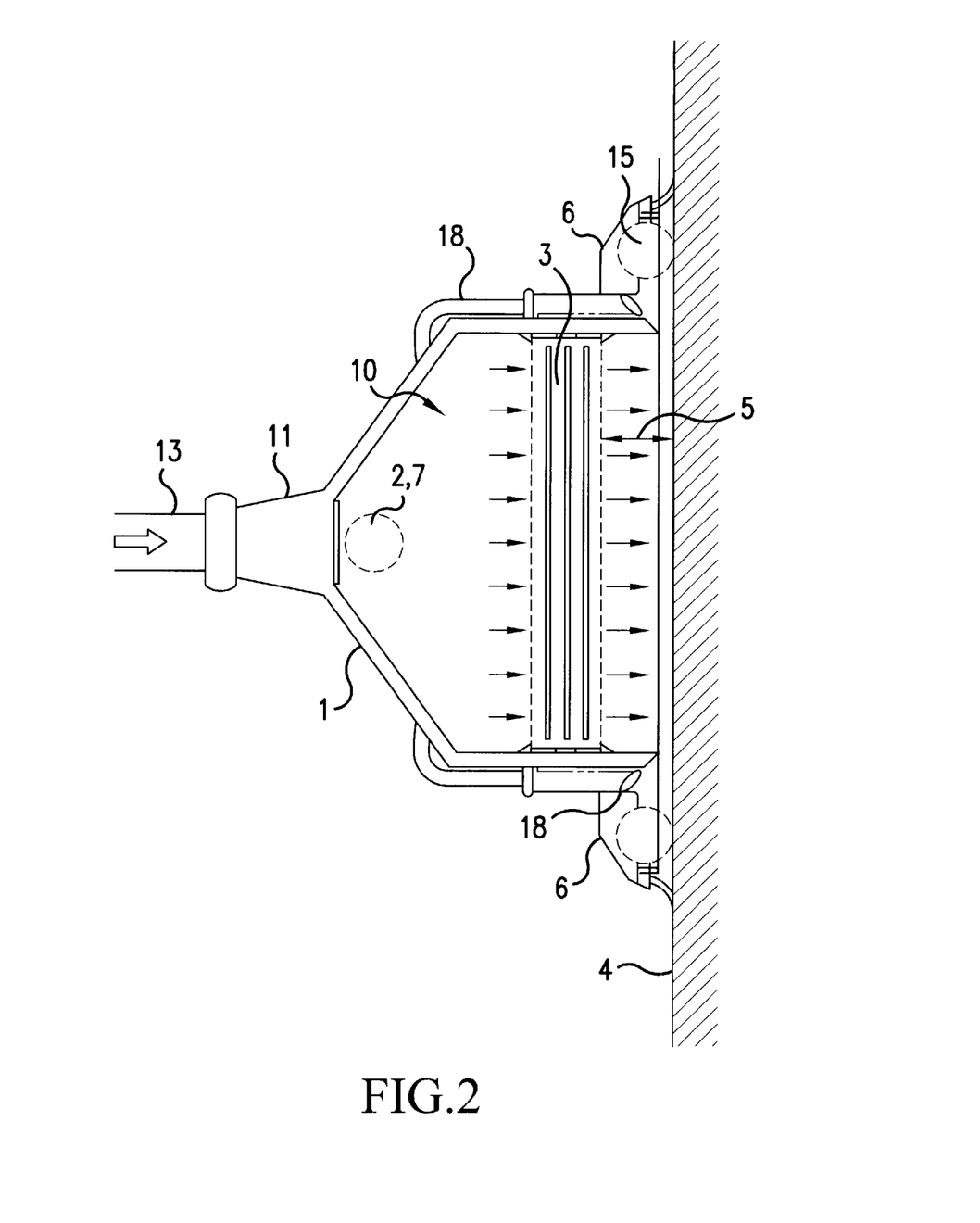
FIG. 2 shows a view of a disinfection head, complete with the nozzle assembly used and suction nozzles at the side, it also shows the formation of a laminar flow.

FIG. 2 shows an aerial view of the steam chamber 5 with a distance of approx. 2.5 cm between the surface to be disinfected 4 and the nozzle assembly 3 opposite. The diagram also shows the suction bell 6 with the sliding bearings 15 running inside it to the side of the disinfection head 1. The suction channels 18 to the side run into the inside of the plastic holder 2 underneath the disinfection head.

The diagram also shows the fact that the nozzle assembly 3 is divided into three plates at a distance of about 1 mm in order to improve the effectiveness of the steam for disinfection.

Figure 3:
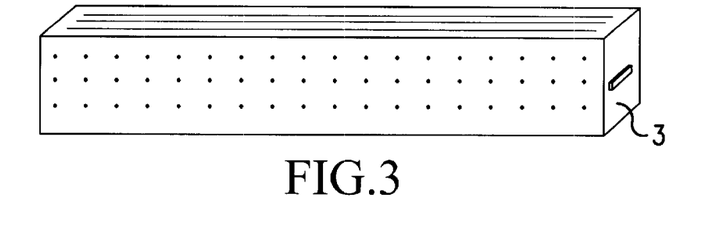
FIG. 3 shows a view of a rectangular nozzle assembly.

FIG. 3 shows, with perspective, the front view of a nozzle assembly 3 to clarify the even distribution of the openings, it also shows a guide at the side, which provides the contact to a heating pipe, which is not drawn in any more detail, and the fact that the nozzle assembly 3 is connected to the disinfection head 1.

Figures 4A, 4B:
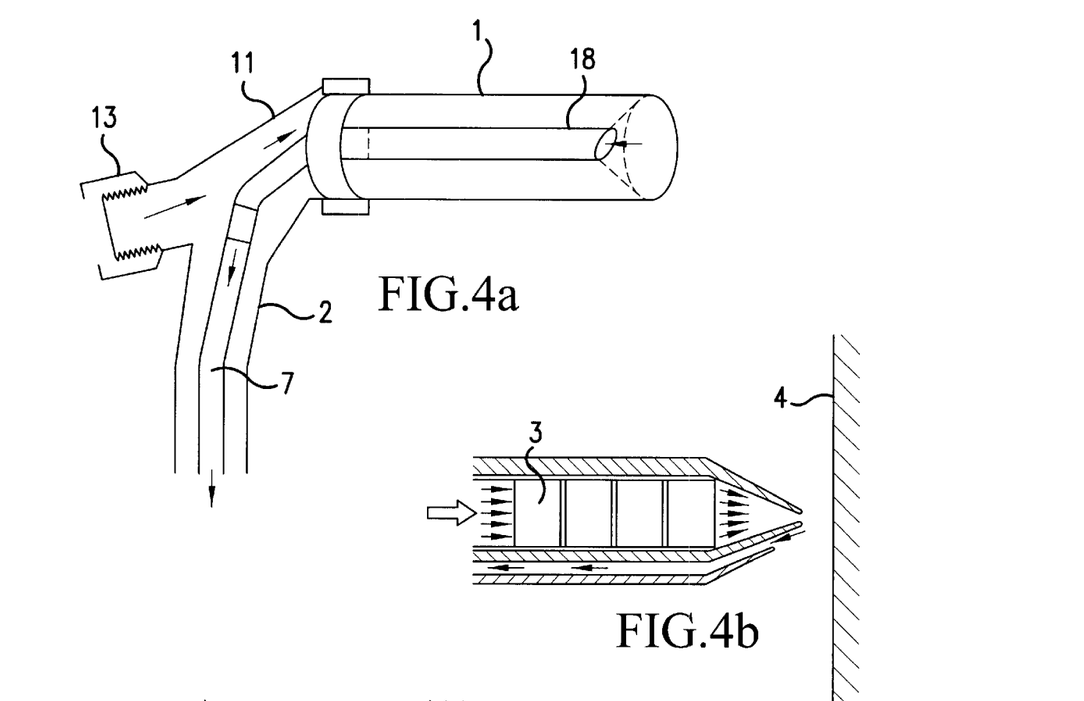

FIG. 4a shows an oval disinfection head 1 with suction channels 18 running along the side, which, in conjunction with a steam inlet spout 11 which has been lengthened accordingly, is used for the disinfection of hoses and pipes.

FIG. 4b shows a disinfection head 1 which is suitable for disinfecting instruments, ventilation grilles and apparatus. The immediate suction of the condensation from the steam, which is very dry anyway due to the use of the nozzle assembly 3 described, means that no dampness is left behind.

Figure 4C:
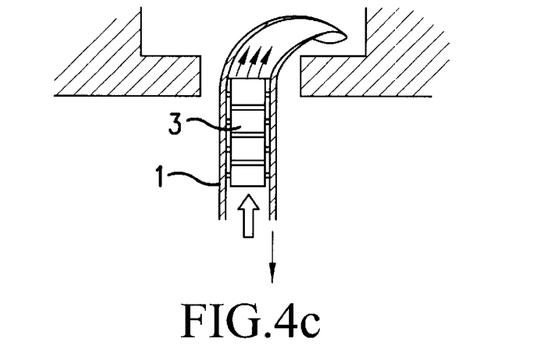

FIG. 4c shows a disinfection head 1 designed to solve a specific problem in infection wards. Many hospitals have suspended perforated ceilings, which are practically inaccessible apart from with a relatively toxic; gaseous mist used for a different disinfection procedure, said celings being used where there are especially strict requirements with respect to the absence of pathogenic micro-organisms. The disinfection head 1 shown here can also be used in overhead cable and pipeline shafts used in particularly important areas, such as the intensive care unit. It transpired that the condensed material already in this sort of shafts could also be sucked away at the same time.

Figure 5:
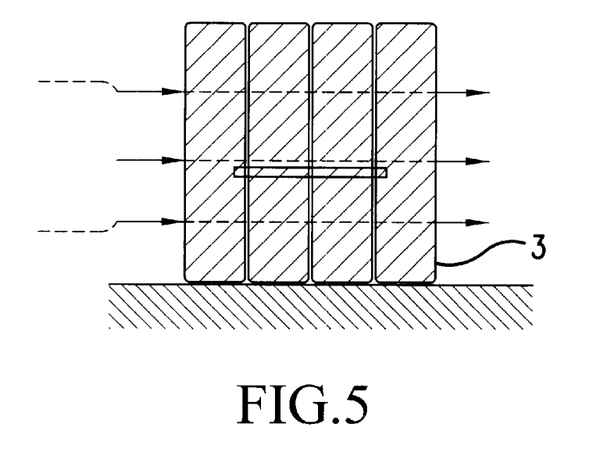
FIG. 5 shows a cross-section of a rectangular nozzle assembly.

FIG. 5 shows the cross-section through a nozzle assembly 3 which is divided into four discs of equal thickness, and the horizontal orientation of the silver-coated openings.

Figure 6:
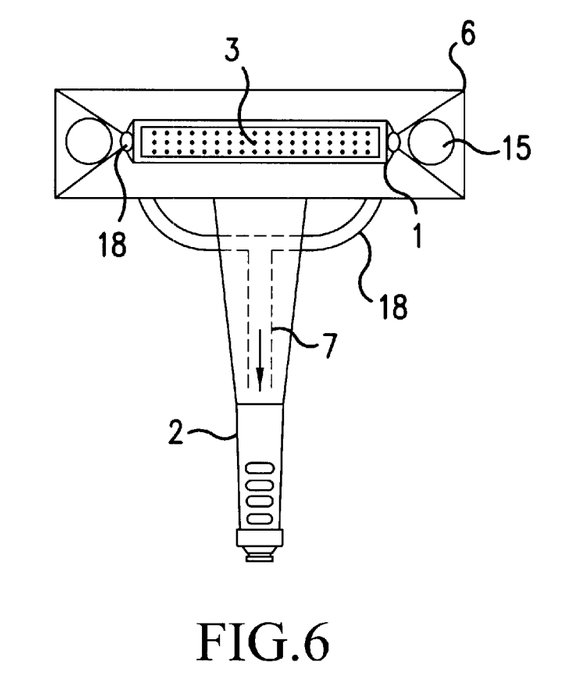
FIG. 6 shows a view of a rectangular disinfection head from underneath.

FIG. 6 shows the disinfection head 1 from underneath. The suction bell 6 which rests on sliding bearings 15 at the side, is preferably made of transparent plastic, and is shaped such as to facilitate the suction of the condensed material into the suction channels 18. The condensed material is then transported further in the suction hose 7.

Figure 7:
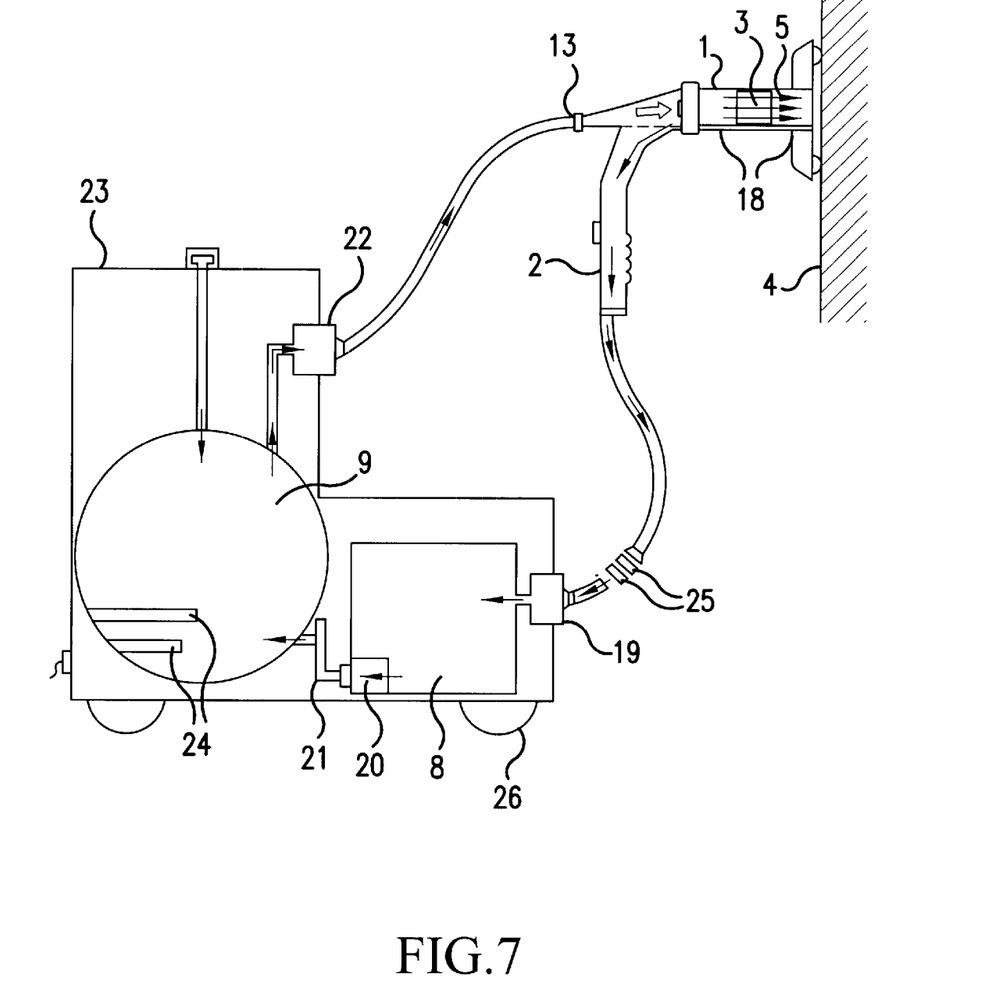
FIG. 7 shows a schematic representation of the combined disinfection and sterilization process.

FIG. 7 shows the complete steam and suction circuit, whereby the steam serves to disinfect and the suction then serves to sterilise.

The steam emitted from the initial evaporator cell 9 is fed through the disinfection head 1 and a nozzle assembly 3, once in the steam chamber 5, it changes its physical state and performs highly concentrated disinfection work in terms of time and location while discharging the energy it was given in the initial evaporator cell 9, it is then sucked through coarse and fine filters 25 by means of two suction pumps 19 and 20, then fed into a collection container 8, from where it is passed via an inlet 21 back into its original location in the initial evaporator cell 9.

The micro-organisms sucked away with the condensed steam, as well as their components or reaction products, are sterilized during the subsequent heating phase in the initial evaporator cell 9.

The individual components, i.e. the initial evaporator cell 9 with the heating elements 2 and a steam outlet valve 22, as well as the collection container 8, which is connected to the initial evaporator cell 9 via an inlet 21, and the suction pumps 19 and 20 are all housed in a mobile unit 23 on wheels 26. The hygienic advantage of the closed circuit are also supported by a high level of user-friendliness and a technology which makes sparing use of the resources of water and energy.

List of Reference Numbers

1 Disinfection head
2 Plastic holder
3 Nozzle assembly
4 Surface to be disinfected
5 Steam chamber
6 Suction bell
7 Suction hose
8 Collection container
9 Initial evaporator cell
10 Preliminary chamber
11 Inlet spout
12 Inlet
13 Inlet hose
14 Plastic band or brush crown
15 Sliding bearings
16 Steam/suction function switch
17 Signal lamp
18 Suction nozzle/channel
19 Suction pump
20 Suction pump
21 Inlet
22 Steam outlet valve
23 Mobile unit
24 Heating elements
25 Coarse and fine filter
26 Wheels

What is claimed is:

1. A process for disinfection of flat and enclosing surfaces using steam which comes into contact with the surface to be disinfected, wherein the steam generated by an initial evaporator cell is fed through a nozzle assembly in a disinfection head and meets the surface to be disinfected, which is at a specific distance away, as steam which is free of any drops of water and with a laminar flow directly from said nozzle assembly, whereby the disinfection head forms a steam chamber with the surface to be disinfected, and, once the steam has condensed, the condensation is sucked away via a suction bell placed over the disinfection head and fed first into a collection contained, then into the initial evaporator cell, where it is sterilized by heating and fed from the initial evaporator cell back to the disinfection head.

2. A disinfection device comprising:
   a disinfection head, a nozzle assembly inserted into said distinfection head, a suction bell connected to suction channels and placed over the disinfection head, said disinfection head being movably attached to a holder, said holder having an inlet hose for the steam and a suction hose interconnected with the suction channels, said inlet hose being interconnected via a steam outlet valve with an initial evaporator cell having heating elements, said suction hose being interconnected with a collection container via a first suction pump, said collection container being interconnected with said initial evaporator cell via a second suction pump and an inlet, wherein said initial evaporator cell, said collection container, said first suction pump, said second suction pump, said inlet, and said steam outlet valve are combined into a mobile apparatus.

3. The device in accordance with claim 2, wherein the nozzle assembly includes several plates which join together to form a carrier, has a thickness of approx. 2.5 cm, has round openings with a diameter of around 0.5 mm across the whole of its surface and is made of plastic or ceramic material.

4. The device in accordance with claim 3, wherein the nozzle assembly can be rectangular or cylindrical and different sizes, and can be heated.

5. The device in accordance with claim 2, wherein external surfaces and vertical internal surfaces of the nozzle assembly are coated with a precious metal.

6. The device in accordance with claim 3, wherein the openings on the nozzle assembly exhibit a vacuum coated precious metal surface.

7. The device in accordance with claim 2, wherein the disinfection head is made of a plastic casing which has an opening to accommodate the nozzle assembly, and opposite the opening there is a steam inlet spout on which the plastic holder, with its steam inlet and its hose connection, rests.

8. The device in accordance with claim 7, wherein the steam inlet spout and therefore the plastic holder are attached to the disinfection head such that they can move.

9. The device in accordance with claim 2, wherein the disinfection head includes a brush or plastic band in the area of the casing around the opening to the surface to be disinfected.

10. The device in accordance with claim 2, wherein the suction bell has sliding bearings or rollers at the point where the suction bell comes into contact with the surface to be disinfected.

11. The device in accordance with claim 2, wherein an automatic time function operated by the user controls the suction function by means of a switch on the holder whereby a lamp displays the effective time for the steam.

12. The device in accordance with claim 2, wherein the suction channels have opening angles which are more than 100 degrees and which are around 2 cm from the surface to be disinfected.

13. The device in accordance with claim 2, wherein the suction channels join up to suction hoses and meet inside the holder to form a single suction hose.

14. The device in accordance with claim 2, wherein condensed material is passed through coarse and fine filters and sucked by the first suction pump into the collection container.

15. The device in accordance with claim 2, wherein the collection container has a lesser volume than that of the initial evaporator cell, whereby a signal indicates when condensed material has reached a certain level.

16. The device in accordance with claim 5, wherein the precious metal is gold or platinum.

17. The device in accordance with claim 6, wherein the precious metal is silver.

18. The device in accordance with claim 8, wherein a ball joint connects the disinfection head to the steam inlet spout and the plastic holder.

* * * * *